United States Patent [19]

Lindqvist et al.

[11] Patent Number: 4,795,461

[45] Date of Patent: Jan. 3, 1989

[54] UV ABSORBING LENS MATERIAL

[75] Inventors: Bengt Lindqvist, Upsala; Bjarne Högström, Sjövde; Martin Sandberg, Upsala; Per I. Nilsson, Tidaholm, all of Sweden

[73] Assignee: Pharmacia AB, Upsala, Sweden

[21] Appl. No.: 873,354

[22] Filed: Jun. 12, 1986

[30] Foreign Application Priority Data

Jul. 19, 1985 [SE] Sweden ............................. 8503522

[51] Int. Cl.$^4$ .......................... A61F 2/16; G02B 5/22; F21V 9/06
[52] U.S. Cl. ........................................ 623/6; 252/589; 523/106
[58] Field of Search ............... 252/588, 589; 523/106; 623/6

[56] References Cited

U.S. PATENT DOCUMENTS

| | | | |
|---|---|---|---|
| 4,304,895 | 12/1981 | Loshaek | 252/588 |
| 4,310,650 | 1/1982 | Gupta et al. | 526/313 |
| 4,390,676 | 6/1983 | Loshaek | 526/313 |
| 4,562,600 | 1/1986 | Ginsberg et al. | 623/6 |
| 4,636,212 | 1/1987 | Posin | 623/6 |

FOREIGN PATENT DOCUMENTS

131468  1/1985  European Pat. Off. ............ 252/588

OTHER PUBLICATIONS

W. T. Ham, "Ocular Hazards of Light Sources...", J. Occupational Medicine, vol. 25(2), 1983, p. 101.

*Primary Examiner*—John F. Terapane
*Assistant Examiner*—Catherine S. Kilby
*Attorney, Agent, or Firm*—Fred Philpitt

[57] ABSTRACT

The invention is concerned with a UV absorbing plastics material to be used in intraocular lenses, said material having been produced by means of incorporating in the plastics monomer mixture, prior to the polymerization thereof, a combination of chromophores selected from two groups of substances.

6 Claims, No Drawings

UV ABSORBING LENS MATERIAL

The present invention relates to a UV absorbing material to be employed in intraocular lenses. The material is produced by incorporating a combination of chromophores selected from two groups of substances in a monomeric mixture prior to polymerization thereof.

A certain portion of the incident sunlight normally falling on the eye is absorbed before it reches the photosensitive cells, whereby the retinal tissue is protected from deleterious short-wavelength radiation. The absorption takes place predominantly in the cornea and the lens, the former absorbing in a wavelength range of up to about 300 nm, and the latter absorbing within a range of up to about 400 nm and in elderly persons up to 450 nm and even higher values. The lens in some cases, where it has undergone morbid changes and lesions of a certain type, is removed by surgery and replaced by an intraocular lens of plastics material; this is usually polymethyl methacrylate (PMMA). However, since plastics materials such as e.g. highly purified PMMA transmit a substantial amount of radiation having wavelengths below 400 nm the substitution of e.g. a PMMA lens for the natural lens involves a major loss of absorption. Recognition of this fact and further studies, which indicated that lesions of the retina were caused by short-wavelength radiation, were conducive to the development of new lens materials which were meant to be as similar as possible to that of the natural lens. To this end UV absorbing components were incorporated in the lens material when the polymerization was carried out; also it has been suggested that the surface of the lens should be coated with some suitable UV absorbing composition.

UV absorbing lens materials which are previously known are described in for example U.S. Pat. Nos. 4,390,676, 4,304,895, 4,310,650, and 3,162,676. They are copolymers of benzophenone derivatives with vinyl monomers of various kinds. Benzotriazole derivatives have also been employed, and methods for producing copolymerizable components selected from this group of substances are described in EP No. 131468.

A characteristic feature common to all the various materials described in these publications and to the commercially available UV absorbing intraocular lenses is that they absorb only radiation of wavelengths below about 400 nm. The so-called "cut-off value" for these types of materials is below 400 nm (see for instance U.S. Pat. No. 4,390,676).

However, a number of articles have been published indicating that also short-wave blue light may cause damage to retinal tissues (see for instance W.T. Ham, Journal of Occupational Medicine Vol. 25(2), 1983, p. 101); but quite evidently none of the aforesaid intraocular lenses provide an adequate absorption of such radiation.

We have now found that a lens composition having the desired properties can be produced by incorporating a combination of components selected from two special groups of substances (group (I) and group (II)) in a lens material known per se consisting for example of a plastics material of the acrylic resin type, such as for instance PMMA or copolymers of methyl methacrylate and ethyl acrylate, prior to polymerization of said material.

Substance group (I) consists of chromophores having absorption maxima within the wavelength range of 330–370 nm, with a molar absorptivity of $0.35 \times 10^4$ to $5 \times 10^4$, especially $0.7 \times 10^4$ to $3.5 \times 10^4$, the spectral bandwidth being within the range of 50–110 nm. These values refer to a liquid medium, for instance the chromophore being dissoved in chloroform or another suitable solvent. Components belonging to this group, as well as components belonging to the below-defined group (II), have to be compatible with a lens polymerization procedure. For instance, they must not undergo any undesired reactions during the polymerization reaction, e.g. such as would cause their capacity of UV absorption to substantially subside or disappear or would result in the formation of reaction products interfering with the optical properties of the material, e.g. so as to produce opalescent portions. Moreover, the solubility of the components of the reaction mixture should be such that the lens produced will not contain any undissolved components.

Substance group (II) consists of chromophores which at a wavelength of 440 nm have a molar absorptivity within the range of $0.1 \times 10^4$ to $2 \times 10^4$.

The lens material of this invention is characterized in that a polished disc of this material having a thickness of 1 mm has the following transmittance properties:

The transmittance
(T) is less than 1% below 380 nm
(T) is less than 10% at 400 nm
(T)=50% at some point in the range of 420–460 nm
(T) is at least 85% above 500 nm
(T) is at least 90% above 550 nm.

Various amounts of chromophores from the two groups could be combined to give the transmittance characteristics specified above. Such combinations could be found by experimental work by a man of skill in the art and who has knowledge of the present invention. Concentrations in the range of 0.005 to 0.3% (w/w) are preferred.

As an example of a substance belonging to group (I) may be mentioned Tinuvin 326 (Ciba-Geigy, Switzerland) having an absorption maximum at about 352 nm and a spectral bandwidth of 90 nm. The molar absorptivity at 352 nm being $1.52 \times 10^4$.

Tinuvin 326 i.e. 2-(5-chloro-2H-benzotriazol-2-yl)-6-(1,1-dimethylethyl)-4-methyl)-phenol has the structure formula (methyl groups only indicated):

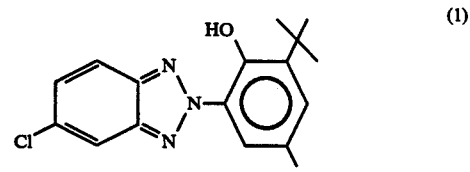

(1)

Group (II) may be exemplified by Macrolex Gelb 3 G (Bayer AG, West Germany) which at a wave length of 440 nm has a molar absorptivity of $1.23 \times 10^4$.

Another example of a substance belonging to group (II) is the azo-compound methyl-2-hydroxy-5-((4-hydroxyphenyl)azo) benzoate with the structure formula:

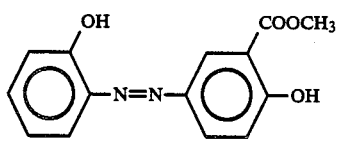 (2)

This compound (2) has a molar absorptivity of $0.45 \times 10^4$ at 440 nm.

An important requirement in the manufacture of intraocular lenses is that the material, i.e. the lens composition, is stable. Accordingly, it is imperative that (i) no components leak from the lens in such amounts that they could give rise to undesirable reactions and (ii) the absorption capacity is duly retained during an expected implantation period of several years.

Thus the invention relates to a synthetic composition for manufacturing intraocular lenses absorbing UV and short wave length visible light, consisting preferably of a plastics material such as e.g. PMMA in which a light absorption active amount of at least one component from each of the aforesaid groups (I) and (II) has been incorporated before the polymerization so that a disc of the final material which has been polished and has a thickness of 1 mm will exhibit the aforesaid transmittance properties.

The invention also comprises the manufacture of a UV absorbing intraocular lens composition by means of adding at least one component of each of groups (I) and (II) to a mixture of monomers, known per se, for example to a solution of methyl methacrylate, this addition being followed by polymerization. The process may be carried out in for instance three steps as follows: The group (I) and group (II) chromophores together with an initiator are dissolved in a small volume of the monomer mixture which is then added to the bulk volume of said mixture, this bulk volume having been heated to a desired temperature within the range of 45°-90° C. When a sufficient degree of viscosity has been obtained a glass cell of proper dimensions is filled with the prepolymer, whereupon the cell is sealed and polymerization is allowed to proceed for about 15-20 hours at said temperature of 45°-90° C. Final polymerization is achieved by raising the temperature to about 125° C. for about two hours. Of course there are other practicable ways of carrying out a polymerization reaction incorporating the aforesaid components in a lens material, such other routes being readily obvious to a person skilled in the field of polymerization techniques.

The invention also comprises an intraocular lens prepared by the use of the composition described above. The manufacture of the lens could be carried out in a manner known per se, for instance from a lens blank consisting of the claimed composition. A workpiece is cut out and shaped on a lathe to attain its desired lens profile. Next the loops and lens body portions are cut out with the aid of a laser beam. The lens could also be prepared by an injection molding technique, given as another example.

The invention also comprises an intraocular lens of the synthetic composition described in this specification.

The examples below illustrate a process for producing a composition for manufacturing intraocular lenses according to the present invention but without in any way limiting the invention.

EXAMPLE 1

3.0 kg of methyl methacrylate (MMA) was weighed out and introduced into a double-wall jacketed glass reactor equipped with a water thermostat. While the reactor was being heated, a 100 ml portion of MMA was withdrawn therefrom and transferred to a septum bottle in which it was mixed with 3.00 g of benzoyl peroxide, 0.45 g of Macrolex-Gelb 3G (Bayer) and 6.00 g of Tinuvin 326 (Ciba-Geigy). This mixture was put back into the bulk of the MMA when the latter had reached a temperature of 80° C., whereupon polymerization was allowed to proceed at this temperature until a $10 \pm 5\%$ degree of conversion had been achieved. The prepolymer was removed from the reactor into a glass cell which was then sealed after expulsion of (any potential) air bubbles. The glass cell was thereafter transferred to a convection furnace having a temperature of 60° C.; reaction there was allowed to proceed for 17 hours. The final polymerization step was performed at 125° C. for two hours. The concentration of the group I chromophore in the product was approximately 0.2% and of the group (II) chromophore approximately 0.02% (w/w).

The product obtained from this experiment exhibited an extremely high finish, coupled with a very low content of inclusions. The molecular weight (weight mean value) was found to be greater than $2 \times 10^6$, the content of residual monomer being $0.4 \pm 0.1\%$.

EXAMPLE 2

(a) Synthesis of methyl-2-hydroxy-5((4-hydroxyphenyl)azo)-benzoate (2).

To a solution of 630 g 2-nitrofenol and 695 ml triethylamine in 3 L of toluene was added 386 ml of methanesulfonylchloride at 15°-20° C. After addition the temperature was raised and kept at 40° C. for 1 h. The mixture was poured into diluted hydrochloric acid and the precipitate was filtered off and washed with hydrochloric acid and toluene. After drying 858 g of product was obtained. From the combined liquid phases the toluene phase was separated and after evaporation of the solvent the residue was leached with warm toluene. The solid material was filtered off, washed with water and toluene and dried and further 140 g was obtained. The combined products were recrystallized from 2.5 L of ice-chilled ethanol, filtered off and then washed with cold ethanol before drying. The yield was 910 g of 2-nitro-methane-sulfonyloxy benzene (3) with m.p. 91° C.

A mixture containing 217 g of (3) and 1 128 g of $SnCl_2 \cdot 2H_2O$ was added to 200 ml of methanol in a 2 L three-necked flask at such a rate that the methanol was kept boiling. The reaction was started by external heating and methanol was added to a final volume of 1 L. The solution was refluxed for 20 min. The methanol was then evaporated and after addition of 200 ml of water the product was poured with efficient stirring into a mixture of 1 760 ml of 50% NaOH, 1 200 ml of $CHCl_3$ and appr. 3.2 kg of ice. The final temperature was 10°-15° C. The chloroform phase was separated and the water phase was extracted with chloroform. The organic phases were pooled and after washing with water and drying with $Na_2SO_4$ the solution (appr. 1.8 L) was diluted with 800 ml of ether and saturated with hydrogen chloride. the precipitate formed was filtered off and washed with ether. After another treatment with ether and hydrogen chloride and subsequent drying in air for 4 h 213 g of 2-methane sulfonyloxy aminobenzene hydrochloride (4), melting point 164°–172° C., was obtained.

223.7 g of (4) was dissolved in 300 ml of water and 100 ml of concentrated hydrochloric acid. The solution was cooled with 600 g of ice and a solution of 69.5 g of NaNO$_2$ dissolved in 150 ml of water, was added with efficient stirring. A solution of 303 g KOH (85%) in 1 L of water was cooled with ice (800 g) and 304 g methylsalicylate was added in one portion. After stirring for 15 s the earlier prepared diazonium salt solution was added in one portion and the solution was stirred for 15 s. After acidification with 200 ml of acetic acid 1 L of chloroform was added. The mixture was heated whereafter the chloroform phase was separated. The water phase was then extracted with chloroform. The combined chloroform phases were washed with water and the chloroform was evaporated. The residue was leached with methanol until the eluate had a pale yellow colour. The synthesis was repeated once in the same scale and once in half scale. All three batches were recrystallized from 4 L of ethylacetate. The yield of methyl (5(-2-methane sulfonyloxy fenylazo)-2-hydroxybenzoate (5) was 479 g with a m.p. of 151° C.

65 g of sodium was dissolved in 2 L of methanol and after addition of 1.4 L of tetrahydrofurane the solution was heated to 60° C. 245 g of (5) was then added to the solution.

After boiling with reflux for 45 min the hot solution was acidified with 170 ml of acetic acid and diluted with 1.5 L of water. The product started to crystallize and after cooling below 10° C. it was filtered off and washed first with 100 ml of methanol and then with water. The methanolysis was repeated in the same scale and the two batches prepared were dissolved, filtered and crystallized from 2.4 L of ethylacetate. After cooling to 5° C. the product was filtered from the solution, washed with 400 ml of methanol and dried in air. The yield of methyl-5(2-hydroxyfenylaza)-2-hydroxy benzoate (2) was 330 g (m.p. 141° C.).

(b) Preparation of a composition for manufacturing intraocular lenses

The experiment was carried out analogously to Example 1. 0.0030 g of the azocompound (2) (synthesized as above), 0.21 g of benzoylperoxide and 0.037 g of Tinuvin 326 (Ciba-Geigy) were dissolved in 20.3 g of methylmethacrylate. The mixture was then heated to 80° C. and the reaction was allowed to proceed until a 6% degree of conversion was obtained. A glass cell was then filled with the prepolymerizate and the polymerization reaction was continued at 60° C. for 16 hours. For the final reaction the temperature was increased to 120° C. and the product was kept at this temperature for 2 hours.

The final product had a mean molecular weight ($M_w$) of about $3.5 \times 10^6$ g/mol. The concentration of the group (I) and group (II) chromophores in the material was approximately 0.2% and 0.01%, respectively.

The transmittance characteristics of this material measured on a polished 1 mm thick sheet was as follows:

| Wavelength (nm) | Transmittance (%) |
| --- | --- |
| 396 | 3,7 |
| 400 | 7,5 |

-continued

| Wavelength (nm) | Transmittance (%) |
| --- | --- |
| 404 | 11,8 |
| 408 | 16,3 |
| 412 | 20,3 |
| 420 | 26,7 |
| 428 | 33,2 |
| 440 | 46,0 |
| 460 | 69,1 |
| 480 | 83,2 |
| 500 | 89,4 |
| 540 | 91,8 |
| 600 | 92,2 |

This experiment relates to the preferred embodiment of the invention.

EXAMPLE 3

In order to test the stability of the lens materials prepared according to the invention a piece of a PMMA composition was immersed in a balanced salt solution (0.9% sodium chloride, 0.01% sodium dihydrogen phosphate and 0.003% sodium lauryl sulfate; sodium hydroxide to pH 7.4)) and irradiated with a 300–400 nm "blacklight" source at an intensity of 1 mW/cm$^2$ for one week. This value should be compared to a normal intensity, from scattered sun light of wavelengths from 300–400 nm, reaching the lens inside the eye, to be about 0.01–0.3 mW/cm$^2$. In this test there was no alteration in transmission characteristics for a PMMA composition prepared analogously to Example 2 and containing 0.02% of component (2) and 0.1% Tinuvin 326.

In a leaching study two ethylene oxide sterilized samples of a PMMA composition containing 0.03% of compound (2) and 0.2% Tinuvin 326, each sample having a surface area of 4 cm$^2$ were leached in 2 ml of balanced salt solutions in glass test tubes (60×16 mm) which were sealed with plastic stoppers. Sample number 1 was leached at 37° C. protected from light, while sample number 2 was leached at 20° C., irradiated during the leaching period as described above (1 mW/cm$^2$). After 14 days the solutions were analysed with a high performance liquid chromatography (HPLC) technique.

Columns: Nucleosil C-18, 10 μm, 4×250 mm and Brownlee Lab C-18, 10 μm, 4×4 mm (for purification of the aqueous phase).

Eluent A: 0.05% formic acid adjusted to pH 3.5 with sodiumhydroxide.
Eluent B: acetonitrile
Flow rate: 2.0 ml/min
Sample volume: 500 /μl

| Gradient program: | |
| --- | --- |
| Time (min) | % A |
| 0 | 100 |
| 10 | 0 |
| 17 | 0 |
| 22 | 100 |

Standard solution: Approximately 4 mg of each chromophore was dissolved in 100 ml acetonitrile. Dilutions were made with water.

The results indicated a concentration of less than 0.01 ppm of compound (2) and less than 0.01 ppm of Tinuvin 326 in the leakage solutions.

The tests carried out clearly demonstrate the stability of the UV-absorbing lens compositions prepared according to the present invention.

We claim:

1. A composition for manufacturing intraocular lenses that absorb UV and short-wave visible light, characterized in that a light absorption active amount of (I) 2-(5-chloro-2H-benzotriazol-2-yl)-6-(1,1-dimethylethyl)-4-and (II) methyl-2-hydroxy-5-((4-hydroxyphenyl)azo)benzoate are added to a monomer mixture suitable for preparing intraocular lenses prior to the polymerization thereof, so that a polished disc of the polymerized composition having a thickness of 1 mm has the following transmission characteristics: the transmittance (T)

is less than 1% below 380 nm, and
    is less than 10% at 400 nm, and
    is equal to 50% at a point within the range of 420 to 460 nm, and
    is at least 85% above 500 nm, and
    is at least 90% above 550 nm.

2. The composition of claim 1 wherein the lens material monomer is methyl methacrylate and the chromophores (I) and (II) are present at concentrations in the range from 0.005 to 0.3% (w/w).

3. An intraocular lens that absorbs UV and short-wave visible light which is formed from a lens composition produced by incorporating in a monomer mixture suitable for preparing intraocular lenses prior to the polymerization thereof a light absorption active amount of (I) 2-(5-chloro-2H-benzotriazol-2-yl) -6-(1,1-dimethylethyl)-4-methyl-phenol and (II) methyl-2-hydroxy -5-((4-hydroxy-phenyl)azo)benzoate.

4. The intraocular lens of claim 3 wherein the lens material monomer is methyl methacrylate and the chromophores (I) and (II) are present at concentrations in the range from 0.005 to 0.3% (w/w).

5. An intraocular lens absorbing UV and short-wave visible light produced by incorporating a mixture of (I) 2-(5-chloro-2H-benzotriazol-2-yl)-6-(1,1-dimethyl-and (II) methyl-2-hydroxy-5-((4-hydroxy-phenyl)azo) benzoate together with an initiator dissolved in a volume of a monomer mixture suitable for preparing intraocular lenses which is then added to the bulk volume of said monomer solution, this bulk volume having been heated to a desired temperature within the range of 45° to 90° C., whereupon the viscous prepolymer so formed is allowed to polymerize at said temperature in a cell, whereafter the temperature is raised for the final polymerization and the lens is prepared from the polymerization product.

6. The intraocular lens of claim 5 wherein the lens material monomer is methyl methacrylate and the chromophores are present at concentrations in the range from 0.005 to 0.3% (w/w).

* * * * *